US012567497B2

(12) United States Patent (10) Patent No.: US 12,567,497 B2
Robson et al. (45) Date of Patent: Mar. 3, 2026

(54) METHOD OF ANALYSING MEDICAL IMAGES

(71) Applicant: Perspectum Limited, Oxford (GB)

(72) Inventors: Matthew Robson, Oxford (GB); Alex Smith, Oxford (GB); Fernandes Carolina, Oxford (GB)

(73) Assignee: Perspectum Limited, Oxford (GB)

( * ) Notice: Subject to any disclaimer, the term of this patent is extended or adjusted under 35 U.S.C. 154(b) by 291 days.

(21) Appl. No.: 18/276,600

(22) PCT Filed: Feb. 11, 2022

(86) PCT No.: PCT/EP2022/053393

§ 371 (c)(1),
(2) Date: Aug. 10, 2023

(87) PCT Pub. No.: WO2022/171807

PCT Pub. Date: Aug. 18, 2022

(65) Prior Publication Data

US 2024/0136052 A1 Apr. 25, 2024
US 2024/0233917 A9 Jul. 11, 2024

(30) Foreign Application Priority Data

Feb. 12, 2021 (GB) .................................... 2101949

(51) Int. Cl.
*G16H 30/40* (2018.01)
*G06T 7/00* (2017.01)
(52) U.S. Cl.
CPC .......... *G16H 30/40* (2018.01); *G06T 7/0016* (2013.01); *G06T 2207/10088* (2013.01)

(58) Field of Classification Search
CPC .................. G16H 30/40; G06T 7/0016; G06T 2207/10088; G06T 5/50; G01R 33/246;
(Continued)

(56) References Cited

U.S. PATENT DOCUMENTS 10,228,432 B2 * 3/2019 Piechnik ............ G01R 33/5673
10,575,771 B2 * 3/2020 Banerjee ................ A61B 5/055
(Continued)

OTHER PUBLICATIONS

Pediatric Radiology, vol. 51, 2021, Dillman Jonathan R et al, "Liver TI relaxation times without and with iron correction: reply to Mozes and Tunnicliffe", p. 501 the whole document.
(Continued)

*Primary Examiner* — Tom Y Lu
(74) *Attorney, Agent, or Firm* — Optimus Patents US, LLC

(57) ABSTRACT

A method of analysing MRI images is described. The method comprising the steps of: acquiring a first medical MR image, and a second medical MR image, of a subject at the same nominal magnetic field strength; analysing the first and second MR images to determine a wT1 map from the first and second images; applying a field strength correction based on modification of the nominal field strength used for the first and second MR image acquisitions, and an iron correction to correct for differences in the iron concentration from a normal level using a T2*map, to the wT1 map from the first and second images to generate a corrected wT1 map; using the corrected wT1 map to determine simulated signals for a subject with normal iron levels, and fitting the simulated signals to a standard cT1 to determine a standard cT1 image for the subject.

18 Claims, 4 Drawing Sheets

(58) Field of Classification Search
CPC .... G01R 33/5614; G01R 33/50; A61B 5/055;
A61B 5/4244
See application file for complete search history.

(56) References Cited

U.S. PATENT DOCUMENTS

| | | | | | |
|---|---|---|---|---|---|
| 11,747,422 | B2 * | 9/2023 | Maier | ................ | G01R 33/5608 |
| | | | | | 324/300 |
| 11,861,827 | B2 * | 1/2024 | Kannengiesser | ...... | G06N 3/045 |
| 11,874,360 | B2 * | 1/2024 | Maier | ................ | G01R 33/5608 |

OTHER PUBLICATIONS

Pediatric Radiology, vol. 51, 2021, Mozes Ferenc et al, "Differences between T1 and corrected T1 cannot be attributed to iron—correction only", pp. 499-500 the whole document.
Pediatric Radiology, vol. 50, 2020, Dillman Jonathan R et al, "Comparison of liver T1 relaxation times without and with iron correction in pediatric autoimmune liver disease", pp. 935-942 the whole document.
Journal of Cardiovascular Magentic Resonance, vol. 15, 2013, Fabio S Raman et al, "Modified look-locker inversion recovery T1 mapping indices: assessment of accuracy and reproducibility between MRI scanners", p. P134 the whole document.
PLOS One, vol. 14, 2019, Bachtiar Velicia et al, "Repeatability and reproducibility of multiparametric magnetic resonance imaging of the liver", p. e0214921 the whole document.
2020, Perspectum, "Our Metrics Understanding cT1", pp. 1-2 URL: https://web.archive.org/web/20201021162229 if /https://perspectum.corn/media/1350/understanding-ctl.pdf the whole document.
Journal of Heptaology, vol. 60, 2014, Banerjee Rajarshi et al, "Multiparametric magnetic resonance for the non-invasive diagnosis of liver disease", pp. 69-77 the whole document.
Magnetic Resonance in Medicine, vol. 52, 2004, Daniel R Messroghli et al, "Modified Look-Locker inversion recovery (MOLLI) for high-resolution TI mapping of the heart", pp. 141-146 the whole document.

* cited by examiner

METHOD OF ANALYSING MEDICAL IMAGES

FIELD OF THE INVENTION

This invention relates to a method of analysing Magnetic Resonance Imaging (MRI) images, to generate a synthetic MRI image, using images from a range of different MRI scanners.

BACKGROUND

Magnetic Resonance (MR) Imaging (MRI) scanning technology can be used to acquire images of the human body that have a contrast that is dependent upon the nuclear magnetic resonance (NMR) relaxation properties of the imaging nucleus (typically the hydrogen atoms in water and fat). It has been known for a long time that these depend on the environment of the atoms yielding these spin properties. The T1, T2 and T2* properties (for example) depend on the magnetic environment of the atoms and also upon the motion of these molecules within this environment.

In non-viscous liquids (such as cerebrospinal fluid (CSF) for example) the hydrogen nuclei of water have long T1 and T2 owing to the uniform magnetic field environment and that rapid unhindered motion of the water molecules. Protons that are bound or interact with proteins have hindered motion and can have much shorter T2 and T1. These relaxation properties have been found to be useful as the ensemble average fluid environment of hydrogen nuclei in fats and water are frequently different in diseased than in healthy tissues.

By collecting a series of images that show the same anatomy but with image contrast with different sensitivity to these relaxation properties it is possible to create parametric maps of the relaxation properties. There are a few challenges to this:

Firstly, the data acquisition is challenging in tissues of the abdomen owing to the dual challenges of cardiac and respiratory motion as the images that are collected benefit from being absolutely aligned. The image acquisitions must somehow freeze the cardiac and/or respiratory motion and this challenge can make the generation of a perfect T1 map for the acquired image difficult.

Secondly, extracting the parametric maps from the acquired images with different contrast can be difficult. This difficulty can be due to the level of noise in the data, the small number of datapoints, complications in the fitting function due to imperfect acquisition or confounding sources of MRI signal intensity.

The applicants have pioneered the use of a T1 based imaging contrast based on T1 as determined by the MOLLI method (Modified Look-Locker Inversion recovery). As iron in the body affects T1, and iron concentration in the liver is highly variable the applicants have used a pioneering approach that corrects the T1 measurement for the image, according to the concentration of iron present in each liver. The applicants call this metric cT1 (corrected T1) and the LMS (LiverMultiScan) product determines maps of cT1 in human livers that are normalised to a standard level of liver iron. The T1 measurement is also dependent on the magnetic field strength of the MRI scanner (typically 1.5T and 3T scanners are used) used to acquire the MR image. The measurements are standardised to what would be achieved on a 3T scanner. Finally, there are some subtle differences between MRI scanners from different manufacturers, therefore values discussed herein are all standardized to measurement on a Siemens 3T scanner. Having a standardized measurement that can be determined for a patient using any of the commercially available scanners that is stable and robust is an important cornerstone for commercial offerings as it potentially enables statements that can be made such as "if your cT1 is above 850 ms then you are in a population that would benefit from a particular treatment" without standardization this simplification is not possible. Parametric mapping using MRI is an intrinsically complicated approach, but it needs to be used in an environment where it needs to be delivered in a simple way, the development of a standardized metric with the potential to deliver ranges for the parameter that lead into stratification decisions (e.g. cT1>825 ms indicates disease and hence the patient should get the drug), which can be used at any MRI centre in the world and is an attractive and scalable technology.

FIG. 1 shows a standard cT1 map derived using the 1.5T MOLLI method with regions of interest highlighted in the figure.

FIGS. 2(a)-2(c) shown images representing cT1, T2* and PDFF (proton density fat fraction) obtained using different image acquisition methods. The T2* and PDFF images are acquired with the multi-echo spoiled gradient echo acquisition. The cT1 is derived from MOLLI.

It should be noted that whilst cT1 is standardized it isn't a good (in a metrological sense) measurement of T1. The MOLLI approach to measurement of T1 depends not just on T1 (as it should) but also on T2, Magnetization transfer, the level of fat in the tissue (PDFF, proton density fat fraction, reported as a percentage of signal from fat compared to the signal from fat+water) and other influences. These deficiencies come from the use of the MOLLI acquisition, which is required to collect data within the time of a short breath-hold and to be gated to the cardiac cycle (this approach can be used in a non-gated fashion in some cases too).

While cT1 is imperfect, it has been used in many studies. This means that it has been validated against biopsy, prognostically and in several clinical trials, therefore whilst it is without a doubt imperfect it does represent something of a standard. Therefore, cT1 is a metric that is of great interest as it has clear relevant correlates even though it is not scientifically pure from an MR physics perspective. It takes many studies to confirm a threshold (such as the 825 ms defined above) and so without a stable method this becomes impossible.

Conventionally cT1 can only be determined from a MOLLI acquisition but this is a limitation for example:

If the scanner doesn't have the MOLLI acquisition method (a common challenge in pharma trials)

If the scanner is unable to support the particular timings needed for the MOLLI sequence to enable accurate cT1 measurement If we are interested in 3D coverage of the liver (MOLLI is a 2D sequence and consequently collecting a 3D volume would require many breath-holds which would be impractical)

If we are interested in collecting very high spatial resolution information (not supported by MOLLI acquisitions)

If the MOLLI sequence couldn't be used owing to problems with breath-holding

If the MOLLI sequence was unreliable owing to spatial variations in B1+ (the RF excitation field) or B0 (the uniformity of the static magnetic field).

In these situations, we would want the information of the cT1 map but would not be able to enable it using the conventional MOLLI based approach.

SUMMARY OF THE INVENTION

According to the invention there is provided a method of analysing MRI images comprising acquiring at least first medical MR image, and a second medical MR image, of a subject at the same nominal magnetic field strength; analysing the first and second images to determine a wT1 map from the first and second MR images; applying a field strength correction based on modification of the nominal magnetic field strength used for the first and second MR image acquisitions and an iron correction to correct for differences in the iron concentration from a normal level using a T2* map, to the wT1 map from the first and second images to generate a corrected wT1 map; using the corrected wT1 map to determine simulated signals for a subject with normal iron levels, and fitting the simulated signals to determine a standard cT1 image for the subject.

Preferably, the inversion time of the first MR image is shorter than the inversion time of the second MR image. Further preferably the time between the acquisition of the first and second medical images is between 0.1-15 seconds. In a further preferred embodiment the time between the acquisition of the first and second images is between 0.1-3 seconds.

In an embodiment of the invention the determination of the wT1 map from the first and second MR images uses a forward Bloch simulation. Preferably, the forward Bloch simulation has inputs comprising one of more of PDFF value, T2 value, wT1 value, a pulse sequence for the scanner used to acquire the images.

In a preferred embodiment of the invention, the analysis of the first and second MR images results in a composite image. Preferably, the wT1 map is determined for the composite image.

In this embodiment of the invention the composite MR image is determined from the first and second images using the following equation: $Sc=real(S_A \times S_B^\dagger)/(abs(S_A^2)+abs(S_B^2))$ Where $\dagger$ denotes the complex conjugate, A is the first image, B is the second image, and C is the composite image.

In an alternative embodiment of the invention, the wT1 is produced using a Variable Flip Angle (VFA) acquisition. Preferably, the VFA acquisition acquires at least two spoiled multiple gradient echo 3D acquisitions with different excitation flip angles. In this embodiment of the invention, the flip angles are between 2° and 30° with a repetition time of less than 20 ms.

Preferably, in this embodiment of the invention the determined wT1 image is calculated from the at least two spoiled multiple gradient echo 3D acquisitions.

In an embodiment of the invention the first and second images are obtained after a single inversion pulse. Preferably, the single inversion pulse is an adiabatic pulse.

Preferably, the method of the invention also comprises the steps of acquiring further medical images immediately before or after the acquisition of the first and second images. Preferably, the further medical images are multi-echo spoiled gradient echo acquisition images.

In an embodiment of the invention, the original first and second MRI images are acquired at 0.3-3.0T.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIG. 2(*b*) shows a T2*image slice acquired with the prior art MOLLI method;

FIG. 2(*c*) shows a PDFF image slice acquired using the prior art MOLLI method;

DETAILED DESCRIPTION

Figure 1:
FIG. 1 shows a cT1 map derived using the 1.5T MOLLI method.
Figures 2A, 2B, 2C:
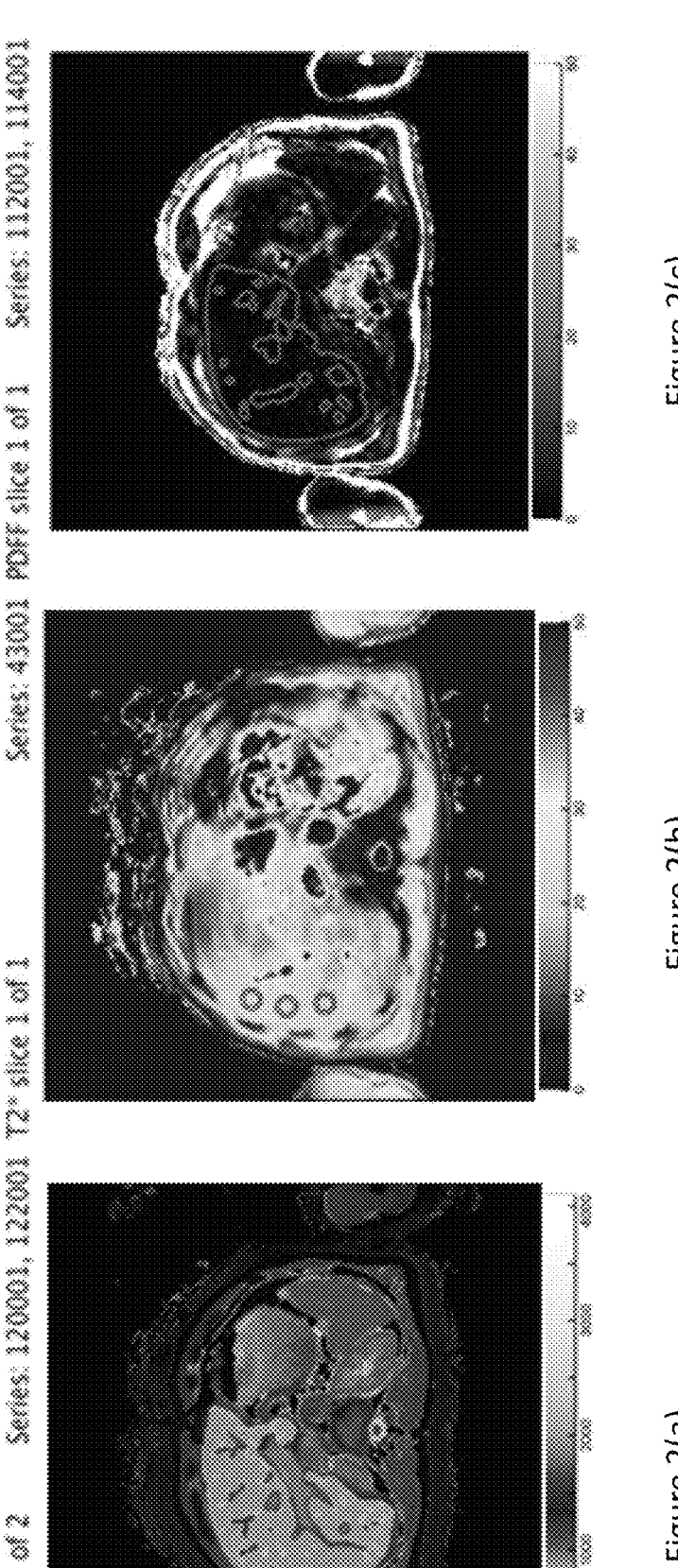
FIG. 2(*a*) shows a cT1 image slice acquired with the prior art MOLLI method.

The present invention will now be described with reference to the accompanying drawings in which there is illustrated an example of a method and apparatus for generating a synthetic cT1 MR image. However, it will be appreciated that the present invention is not limited to the specific examples herein described and as illustrated in the accompanying drawings.

In this first embodiment of the invention a Siemens 1.5T Aera MRI scanner was used to acquire a 2D T1 map, although other scanners with different magnetic field strengths may also be used. For Example, the MRI scanner may operate between 0.3-3T. The methods by which this was performed were as follows. The subject was placed in the scanner using a phased array abdominal coil and a spine array.

In this first embodiment of the invention, dual Inversion recovery Turbo-Flash acquisition is used for MR image acquisition. In this method, 2 snapshot spoiled-gradient echo images (first and second MR images) were acquired after a single inversion pulse within a single <8 second breath-hold. The time between the acquisition of consecutive MR images is typically between 0.1-15 seconds, but more preferably between 0.1-3 seconds This acquisition of the 2 MR images within a single inversion pulse is labelled as NOLLI (Non-mOLLI). These acquisitions yielded pixels of 2×2×6 mm. A single MR image slice was acquired in each breath-hold. In a preferred embodiment of the invention, the acquisition of the MR image used an echo time 4.74 ms. In other embodiments of the invention the echo time for the image acquisition may be in the range 0.5-10 ms. It may be beneficial for the image acquisition echo time to be a time where the fat and water signals are in-phase or approximately in-phase with each other (4.74 ms at 1.5T, 2.37 ms at 3T, although any integer multiple of these times would also work). So short echo times that are a multiple of 4.74 ms are preferred. The inversion pulse was adiabatic (insensitive to B1 inhomogeneity) and two TI's (inversion times) were used and the images acquired at the two inversion times were labelled A (shorter TI) and B (longer TI), these TI values had been previously optimized to ensure good sensitivity to $T_1$ under the expected imaging conditions. Typically, the inversion time, TI, is in the range from 300 ms to 5000 ms, and the TI value for each of the two MR images is difference. The values of TI are designed to optimise the sensitivity to the particular tissue of interest. In this embodiment of the invention a first and second medical MR images are used for the subsequent analysis to determine wT1 map, and using this to generate a corrected wT1 map, and then using this to generate a standard T1 image. In an alternative embodiment of the invention, multiple MR images, e.g. eight images may be used in the analysis to determine the intermediate wT1 map.

Additionally, the standard MR images required for an LMS (LiverMultiScan) acquisition were also collected (i.e. MOLLI-T1, LMS-MOST (for iron) [a multi-echo spoiled gradient echo acquisition], LMS-IDEAL (used for fat in this case) [a multi-echo spoiled gradient echo acquisition]).

A MOLLI-T1 MR image was acquired using a 5-(1)-1-(1)-1 acquisition scheme with 35 deg excitation pulses and a balanced bSSFP (balanced steady state free precession) readout, the MR image acquisition was cardiac gated with an image slice thickness of 6 mm and image acquisition required around 10 seconds (less than the time for 10 heart-beats). The LMS-MOST image acquisition acquires thin slice (3 mm) spoiled gradient echo images with multiple echo times. It is designed specifically to measure the T2* in the liver and is robust to breathing and B0 artefacts through the use of multiple repetitions of the same MR image (7 at 1.5T) that are selectively combined to minimise variance and by using a thin slice that minimises through slice dephasing, the imaging time for the LMS-MOST acquisition is around 10 seconds. The LMS-IDEAL image acquisition also uses a multiple echo spoiled gradient echo acquisition with a low excitation flip angle to minimise differential T1 weighting between the fat and water species and so yield a precise PDFF map (after processing).

Figure 3:
FIG. 3 illustrates a composite image formed from two medical scan images using an embodiment of the invention.

In an embodiment of the invention, for the NOLLI dataset for first and second MR images A and B acquired as described above, the data were read into Matlab (Mathworks, Natick, MA). A composite image (C) was determined from MR images (A and B) as $$Sc = \mathrm{real}(S_A \times S_B^\dagger)/(\mathrm{abs}(S_A^2) + \mathrm{abs}(S_B^2)) \qquad \text{Equation 1}$$

Where † denotes the complex conjugate. Alternatively, T1 may be calculated using a general modelling approach using information from MR images A and B FIG. 3 shows the output from NOLLI image acquisition of the first embodiment of the invention, and initial processing of the acquired MR images to produce a composite image for the subject, from the original images A and B. As described above, the first and second MR images were acquired using Siemens 1.5T scanner, using the acquisition process outlined above. The composite image C, was generated using Equation (1).

A map of the NOLLI-T1 (T1 as determined by NOLLI method) was determined from the composite image C. PDFF (determined from the image acquired by LMS-IDEAL acquisition) and T2 (determined via the T2* from the LMS-MOST acquisition) were also calculated for the composite image C. NOLLI-wT1 (water T1 as determined by the NOLLI method) was determined by simulating the forward Bloch simulation and selecting the wT1 that best explain the data.

The Bloch simulation forward simulation approach used here evaluates what signals would be measured by an MRI scanner given different sample MRI characteristics. This forward Bloch simulation takes as its inputs one or more of a PDFF value, a T2 value, a water-T1 value, and the exact pulse sequence that has been implemented on the particular MRI scanner, it starts at time=0 with a fully relaxed magnetization vector (Mz=1, Mx=0, My=0) and for short time increments (typically 50 microseconds) evaluates how the magnetization vectors are impacted by the effects of RF pulses, off-resonance effects, spoiling gradients and spin relaxation (T1 and T2). At points in time when the signal would be sampled in the imaging sequence the simulated magnetization vector is recorded. The fat and water signals are simulated separately, and combined in proportion to the PDFF. The simulation is run for different water-T1 values as input and the resulting simulated data are recorded. The NOLLI-wT1 is determined as the water-T1 input that corresponds to simulated data that most closely agree with those data that are acquired on the scanner. This matching of the simulated solutions to the acquired data can be done using Sc as the metric, or can be based on other schemes (the ratio of $S_A$ to $S_B$ for example).

The T2(x,y,z), wT1(x,y,z) and PDFF(x,y,z) maps could be collected on any MRI scanner at any field strength, and still be used to determine the composite image of this invention. These parameters could be mapped to their equivalent values at 3T (after acquisition at 1.5T) and registered to one another, to account for slight patient motion and differences in acquisition spatial resolution. Further the spatial T2 (or T2*) is then used to generate a correction for the wT1 to yield a wcT1 (water corrected T1). This will be a water T1 that has been corrected for the impact of iron in the liver.

The PDFF map may be calculated from a single image slice, a single voxel of an image slice (with spectroscopy), multiple image slices or a full 3D volume. In practice the variation in PDFF over a liver in many situations (homogeneous liver diseases) can be fairly small and so it would likely be possible to use a single value of PDFF in these simulation of the signals, but maps of PDFF might also be used. It might be necessary to perform image registration of PDFF maps to the other maps when performing the simulation of the signals.

Figure 4:
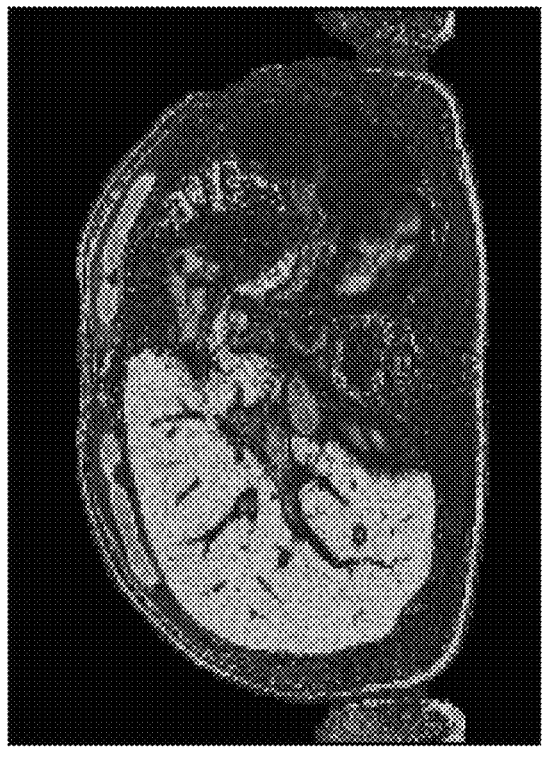
FIG. 4 shows a water T1 (wT1) for the subject of the composite image of FIG. 1.

FIG. 4 shows a wT1 map (a parametric map of the water T1) of liver obtained for the original subject, using the embodiment of the invention, and shows the expected uniformity in the organ of interest in the subject. As shown, there is no impact of fat in this map as fat is taken into account in the fitting of these data. The data used to produce this image was acquired on a Siemens 1.5T scanner. Regions outside the liver will not be correctly mapped. Regions containing flowing blood are impacted by flow artefacts in this method. Masking has been used to remove background noise. Various approaches to masking can be used and none are critical to this invention. In this case a mask was generated based on a machine learning algorithm that replicates the performance of a manually drawn mask around the liver, a manual approach could have been used but the machine learning approach is used for reasons of efficiency.

In an additional embodiment of the invention a wT1 map is produced using a VFA (variable flip angle) acquisition approach which typically acquires 2 or more spoiled gradient multiple echo 3D acquisitions with different excitation flip angles (typically between 2 and 6 degrees, with 3 degrees as a preferred embodiment and between 10 and 30 degrees for the other flip excitation angle, with 15 deg in a preferred embodiment of the invention) both with a short repetition time (TR typically <20 ms, although some embodiments of the invention may have a repetition time greater than 20 ms). For each of these acquisitions two (or more) MR images are acquired and the signal from these echoes is decomposed into fat and water images. The wT1 can be determined as the T1 that best explains the relative intensity of the signal in the water images at the different flip angles. This approach uses a dictionary fitting approach whereby the signals that would have been collected are simulated using a Bloch equation for different water T1, and the water T1 that corresponds to the signal ratio that best matches the signal ratio in the acquired data is used. This simulation can account for signal contributions from fat signal when that additional signal is present (i.e. when fat suppression does not remove all the fat signal), the amount of fat to include in the simulation would be determined from the PDFF map (as described earlier).

For all VFA approaches, a B1+ map (a map of the RF excitation field) is also determined, as whilst this should be spatially uniform and known in practice it is not and it has a large biasing effect on the T1 measured using VFA methods if not corrected.

In an embodiment of the invention, a separate T2* map is acquired and used to determine a T2 map, that is used when fitting the wT1 map. T2* can be used for this purpose because the dominant source of variance in T2 is due to different levels of iron accumulation in the liver, iron is measured accurately with a T2* map. T2* maps are much easier to collect than T2 maps for reasons of acquisition speed (T2 maps typically require >10 minutes to collect, whereas T2* maps can be collected in 10 seconds). In some diseases the assumption of uniform iron distribution in the liver could be used and a single ROI could be used in the simulations (as PDFF above), but alternatively a 2D or 3D map of T2* could be used and the fitting function could be performed on sub-regions or individual pixels of the image.

For the LMS acquisition, data were fit using the LMS Discover tool (in Matlab) that has the same general performance characteristics as the LMS Medical Device but has additional flexibility for rapid prototyping exploratory work.

Taking the measurement of iron and PDFF (fat) from the LMS Discover processing and the NOLLI-wT1 map the cT1 was determined that would have been measured had the sample had normal level of iron and had been scanned on a Siemens 3T scanner using the MOLLI method. In this invention, T2 is standardized to 23.1 ms at 3T for ease of calculation. Of course, other values may be used for alternative standards.

This was performed by firstly correcting the measured NOLLI-wT1 for the impact of iron, then by calculating the wT1 that the tissue would have if it were at 3 Tesla (rather than the 1.5T that the data were acquired). The iron correction is performed by determining the iron concentration using the T2* map and the B0 field strength, and then using a known equation. $(R1(3T)=R1_0(3T)+HIC\times0.029$ g/mg·s; where $R1=1/T1$, and HIC is the hepatic iron concentration) to determine the effects on T1 due to the differences in iron concentration from the normal level.

The field correction is based on empirically determined mappings of the impact of field strength on T1 and is evaluated from a group of subjects scanned at each field strength. In this embodiment of the invention the field correction could be performed before or after iron correction.

Once this field strength and iron corrected water T1 has been calculated, this corrected wT1 value along with the PDFF is used in a Bloch equation simulation of the MOLLI sequence to determine the signals that would be expected if this subject had normal iron levels (in this case represented by a T2* at 3T of 23.1 ms), this standardization is not modified for subject weight, age or sex. If the PDFF was not included in the simulation then this would be a value standardized for a person with normal iron, a heart rate of 60 bpm and with no body fat. The Bloch equation simulation of the MOLLI sequence takes the iron and field strength corrected water T1, the PDFF, and the exact pulse sequence that has been implemented on the reference Siemens 3T scanner. The Bloch equation simulation starts at time=0 with a fully relaxed magnetization vector (Mz=1, Mx=0, My=0)

and for short time increments (typically 50 microseconds) evaluates how the magnetization vector is impacted by the effects of RF pulses, off-resonance effects, spoiling gradients and spin relaxation (T1 and T2). At points in time when the signal would be sampled in the imaging sequence the simulated magnetization vector is recorded. The fat and water signals are simulated separately, and combined in proportion to the PDFF.

Preferably, the forward Bloch simulation uses the known characteristics of the pulse sequence of the 3T reference MRI scanner, and this is performed in a simplified manner for each pixel in turn and would yield a series of simulated signals at each pixel. We simulate using a synthetic heart-rate of 60 beats per minute and for pixels where PDFF >30% we would fix the PDFF to 30%. These values are chosen as standard parameters, although other values may also be used as standardization parameters. The fat would be simulated using the standard 6-peak fat model that is known to represent hepatic fat. Further, the T2 relaxation of the water would be fixed to the T2 of liver with a normal level of iron. The fat and water signals would be combined using the known concentrations from the PDFF(x,y,z) map (this could be position dependent or a global measurement could be used). The MOLLI sequence collects 7 or more images each at different Inversion Time (TI), and so we would result in an array of signals S(TI,x,y,z).

Finally, these simulated MOLLI signals obtained are fed into a standard LMS cT1 fitting pipeline (with normal iron levels, as iron has already been corrected) that determines the cT1. That is, the resulting S(TI,x,y,z) matrix would be fit at each pixel to yield a map of cT1(x,y,z). This cT1 should be equivalent to the cT1 derived using the super-standardized MOLLI methods, which is known to be standardized for field strength and MRI vendor. This final fitting step performs a pixel-by-pixel least-squares fit of the function:

$$S(TI)=(A-B\ \exp(-TI/T_1*)$$

And determines T1 as $$T1=T1*((B/A)-1)$$

In the usual manner for fitting of MOLLI data, either by building a dictionary of varying A, B and T1* and building fit functions for each of these in a dictionary, and then seeing which one best represents the data (perhaps via a least squares estimate, or comparison of the two curves through choosing the combination with the maximum of the dot product of the normalized data with the normalized dictionary). Alternatively, A, B and T1* can be fit using a iterative search approach (i.e. minimised least squares and Levenberg-Marquart), in practice this fitting is not difficult to perform using standard approaches. Once A, B and T1* are known T1 can be determined. In this case the S(TI) have been generated in a manner to ensure that the resulting T1 is standardized to cT1. his processing yields a standardized cT1 measurement.

It would be expected that there would be some small (~5%) systematic difference between this modelling approach and the direct MOLLI acquisition approach. There are several sources for these offsets, most obviously Magnetization Transfer effects, but also subtle bias in wT1 mapping. We would apply a fixed offset to the cT1 for each acquisition pipeline based on comparing human data acquired using the known systems and by this approach. Each pipeline of acquisition (as described above) would need a specific calibration with the goal of these methods delivering the same value for subjects with a cT1 of 825 ms, by modelling for the impact of fat, iron etc. it would be possible to use a single offset per scanner and for the cT1 from different scanners to be reliably standardized across of a range of fat, iron, wT1 etc. This offset might be applied to cT1, but it also might be applied to a different parameter to get the same effect (e.g. wT1).

Figure 5:
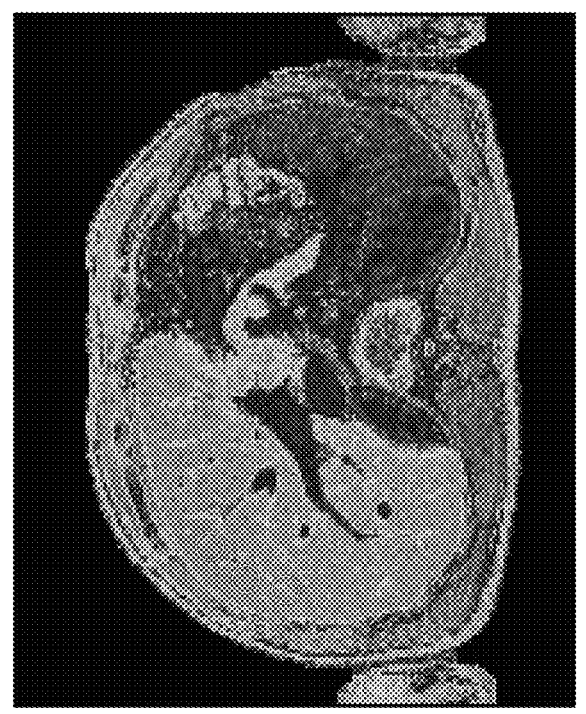
FIG. 5 shows the cT1 map derived from the images in FIGS. 1 and 2.

FIG. 5 illustrates cT1 image using the NOLLI acquisition at 1.5T and mapped into cT1 at 3T using the described novel approach. The cT1 map derived from the NOLLI data with ROI positions shown for the subject. Data from a Siemens 1.5T scanner. 3×ROI=629, 624, 663 ms. These are shown as highlighted circles in the image. The Pooled median in the image for cT1=640+/−51 ms. Typically the pooled median is used, but other metrics such as mean, median, pooled mean may also be used, however pooled median is preferred as this is more robust. Mapping algorithms are only applicable for regions within the liver, regions outside the liver are not correctly mapped.

In the embodiment of the invention as described the image processing could be performed at different dimensions. For example the method of the invention it could be applied at the level of a single large voxel (as in spectroscopy) or over a single region of interest, it could be applied on a pixel by pixel basis over a 2D image, or it could be applied on a pixel by pixel basis over an entire 3D volume. Preferably, the most likely use cases would be to generate cT1 maps in a single 2D slice, in multiple 2D slices or over a 3D volume.

This novel acquisition and processing pipeline is able to deliver synthetic images that demonstrate similar spatial uniformity to the standard LMS MOLLI approach. The quantitative values determined with the novel acquisition and processing pipeline yield values that are consistent with the standard LMS MOLLI approach. Therefore, the novel acquisition and processing pipeline provides a mechanism to deliver a surrogate approach to LMS MOLLI cT1. A further advantage of this invention is that a cT1 map can be obtained from any MRI scanner, irrespective of the magnet strength of the scanner, or the company who have produced the scanner. In addition, the cT1 obtained using the invention maybe more reproducible, or have a higher spatial resolution, or possess some other characteristics than meant the synthetic cT1 obtained with the invention is superior to cT1 as determined with the prior art MOLLI acquisition technique.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system.

The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims. Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

The invention claimed is:

1. A method of analysing MR images comprising:

acquiring a first medical MR image, and a second medical MR image, of a subject at the same nominal magnetic field strength;

analysing the first and second MR images to determine a water T1 (wT1) map from the first and second MR images;

applying a field strength correction, based on modification of the nominal magnetic field strength used for the first and second MR image acquisitions, and an iron correction to correct for differences in the iron concentration from a normal level using an effective T2 (T2*) map, to the wT1 map from the first and second images to generate a corrected wT1 map;

using the corrected wT1 map to determine simulated signals for a subject with normal iron levels, and fitting the simulated signals to a standard corrected T1 (cT1) map to determine a standard cT1 image for the subject.

2. A method according to claim 1, wherein an inversion time for the acquisition of the first MR image is shorter than an inversion time for the acquisition of the second MR image.

3. A method according to claim 1, wherein the time between the acquisition of the first and second medical MR images is between 0.1-15 seconds.

4. A method according to claim 3, wherein the time between the acquisition of the first and second MR images is between 0.1-3 seconds.

5. A method according to claim 1, wherein the determination of the wT1 map from the first and second MR images uses a forward Bloch simulation.

6. A method according to claim 5, wherein the forward Bloch simulation has inputs comprising one of more of proton density fat fraction (PDFF) value, T2 value, wT1 value, a pulse sequence for the scanner used to acquire the images.

7. A method as claimed in claim 5, wherein the analysis of the first and second MR images results in a composite MR image.

8. A method as claimed in claim 7, wherein the wT1 map is determined from the composite MR image.

9. A method according to claim 7, wherein the composite MR image is determined from the first and second MR images using the following equation:

$$SC = \mathrm{real}(S_A \times S_B\dagger)/(\mathrm{abs}(S_A{}^2) + \mathrm{abs}(S_B2));$$

where $\dagger$ denotes the complex conjugate, 2 denotes the square, SC is the data of the composite MR image, SA is the data of the first MR image, and SB is the data of the second MR image.

10. A method as claimed in claim 1, wherein the wT1 map is produced using a Variable Flip Angle (VFA) acquisition.

11. A method according to claim 10, wherein the VFA acquisition acquires at least two spoiled multiple gradient echo 3D acquisitions with different excitation flip angles.

12. A method according to claim 11, wherein the flip angles are between 2-60 and 10-300 with a repetition time of less than 20 ms.

13. A method according to claim 10, wherein the determined wT1 map is calculated from the at least two spoiled multiple gradient echo 3D acquisitions.

14. A method as claimed in claim 1, wherein the first and second MR images are obtained after a single inversion pulse.

15. A method according to claim 14, wherein the single inversion pulse is an adiabatic pulse.

16. A method according to claim 1, further comprising:
   acquiring further medical MR images immediately before or after the acquisition of the first and second images.

17. A method according to claim 14, wherein the further medical MR images are multi-echo spoiled gradient echo acquisition images.

18. A method according to claim 1, wherein the original first and second MR images are acquired at a nominal magnetic field strength of 0.3-3.0 T.

* * * * *